United States Patent
Woloschek et al.

(10) Patent No.: US 6,442,228 B1
(45) Date of Patent: Aug. 27, 2002

(54) DATA ACQUISITION MODIFICATIONS FOR IMPROVED RECONSTRUCTION WITH CONVENTIONAL CT

(75) Inventors: Steven J. Woloschek, Franklin; Kenneth G. Dunahee, Muskego, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/553,192

(22) Filed: Apr. 20, 2000

(51) Int. Cl.$^7$ .................................................. A61B 6/03
(52) U.S. Cl. ............................................ 378/8; 378/95
(58) Field of Search .......................... 378/4, 8, 17, 94, 378/95

(56) References Cited

U.S. PATENT DOCUMENTS

| | | | |
|---|---|---|---|
| 5,489,782 A | | 2/1996 | Wernikoff .................... 250/369 |
| 5,612,985 A | * | 3/1997 | Toki et al. ....................... 378/4 |
| 5,632,968 A | | 5/1997 | Goldenberg ............... 424/1.49 |
| 5,724,037 A | | 3/1998 | Lee ............................. 341/143 |
| 5,799,054 A | * | 8/1998 | Hum et al. .................... 378/17 |
| 5,832,051 A | | 11/1998 | Lutz ............................... 378/8 |
| 5,991,356 A | * | 11/1999 | Horiuchi et al. ................ 378/8 |
| 6,088,611 A | | 7/2000 | Lauterbur et al. .......... 600/407 |
| 6,233,478 B1 | | 5/2001 | Liu ............................. 600/428 |
| 6,252,924 B1 | * | 6/2001 | Davantes et al. .............. 378/8 |
| 6,256,368 B1 | * | 7/2001 | Hsieh et al. .................... 378/8 |
| 6,275,560 B1 | * | 8/2001 | Blake et al. .................... 378/8 |

* cited by examiner

Primary Examiner—David P. Porta
Assistant Examiner—Therese Barber
(74) Attorney, Agent, or Firm—Carl B. Horton, Esq.; Armstrong Teasdale LLP

(57) ABSTRACT

One embodiment of the present invention is a method for imaging an object with a computed tomographic (CT) imaging system that includes steps of scanning an object with a beam of radiation from a CT imaging system to produce a view stream including attenuation data for the object being scanned; sensing one or more dynamic parameters relating to at least one of the object being scanned and the CT imaging system; and integrating information relating to the one or more sensed dynamic parameters into the view stream.

This embodiment integrates information necessary for compensating reconstructed images directly into the view stream, thereby making the necessary information more conveniently available for such compensation.

18 Claims, 3 Drawing Sheets

DATA ACQUISITION MODIFICATIONS FOR IMPROVED RECONSTRUCTION WITH CONVENTIONAL CT

BACKGROUND OF THE INVENTION

This invention relates generally to computed tomography (CT) imaging, and more particularly methods and apparatus for producing dynamically compensated CT images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Known CT imaging system scans include acquisition information and view information. "Acquisition information" includes patient, scanning, and reconstruction information that is static in nature. "View information" is actual attenuation data collected by a detection system of the CT imaging system and is dynamic in nature. In known CT imaging systems, compensation for dynamic changes from a patient or a scanning environment cannot be performed from present, view stream information alone. Thus, blurring in reconstructed images sometimes occurs. For example, images in fluoro CT applications are blurred during tilting of the gantry. Also, helical scans of different portions of a body using different helical pitches now require separate scans, because it is difficult to produce good images during speed transitions or even to compute actual image locations.

It would therefore be desirable to provide convenient methods and apparatus for compensating CT images for dynamic changes from a patient or scanning environment. It would further be desirable to provide such methods and apparatus for utilizing a view stream to provide the compensation information.

BRIEF SUMMARY OF THE INVENTION

In one embodiment of the present invention, there is thus provided a method for imaging an object with a computed tomographic (CT) imaging system that includes steps of scanning an object with a beam of radiation from a CT imaging system to produce a view stream including attenuation data for the object being scanned; sensing one or more dynamic parameters relating to at least one of the object being scanned and the CT imaging system; and integrating information relating to the one or more sensed dynamic parameters into the view stream.

The above-described embodiment integrates information necessary for compensating reconstructed images directly into the view stream, thereby making the necessary information more conveniently available for such compensation.

DETAILED DESCRIPTION OF THE INVENTION

Figure 1:
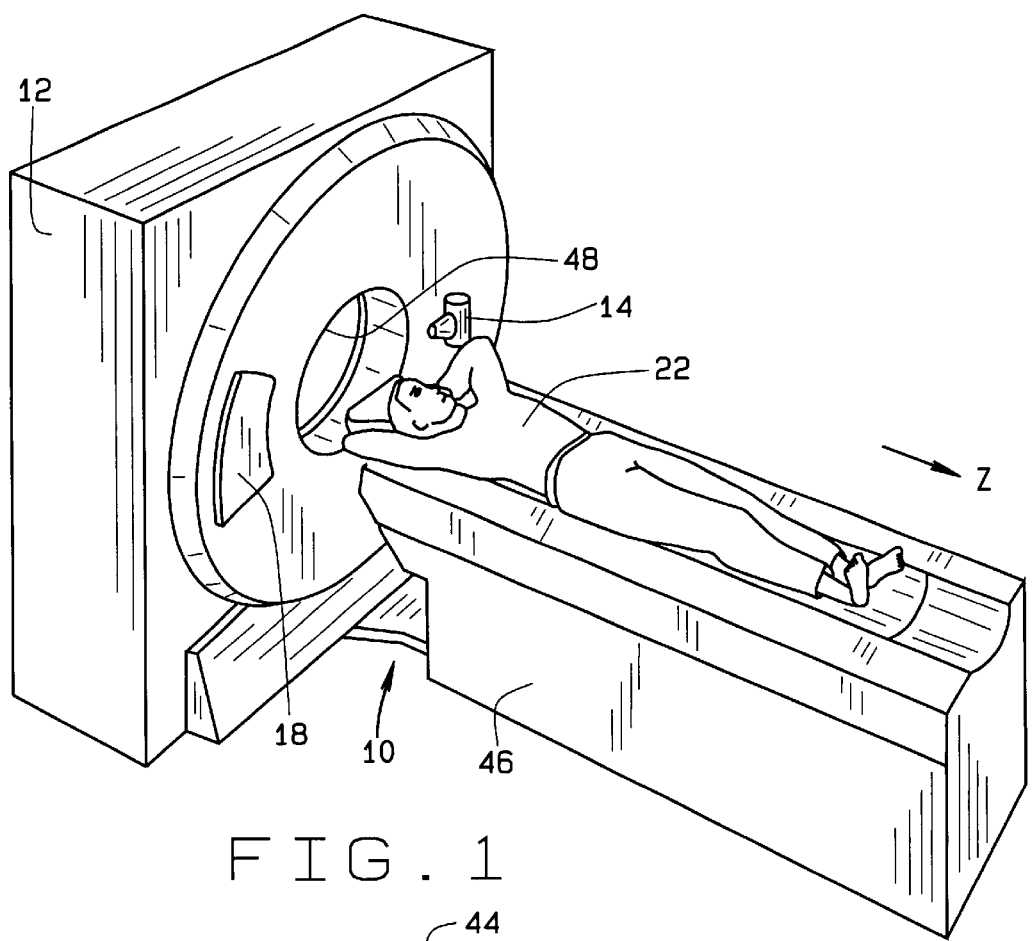
FIG. 1 is a pictorial view of a CT imaging system.
Figure 2:
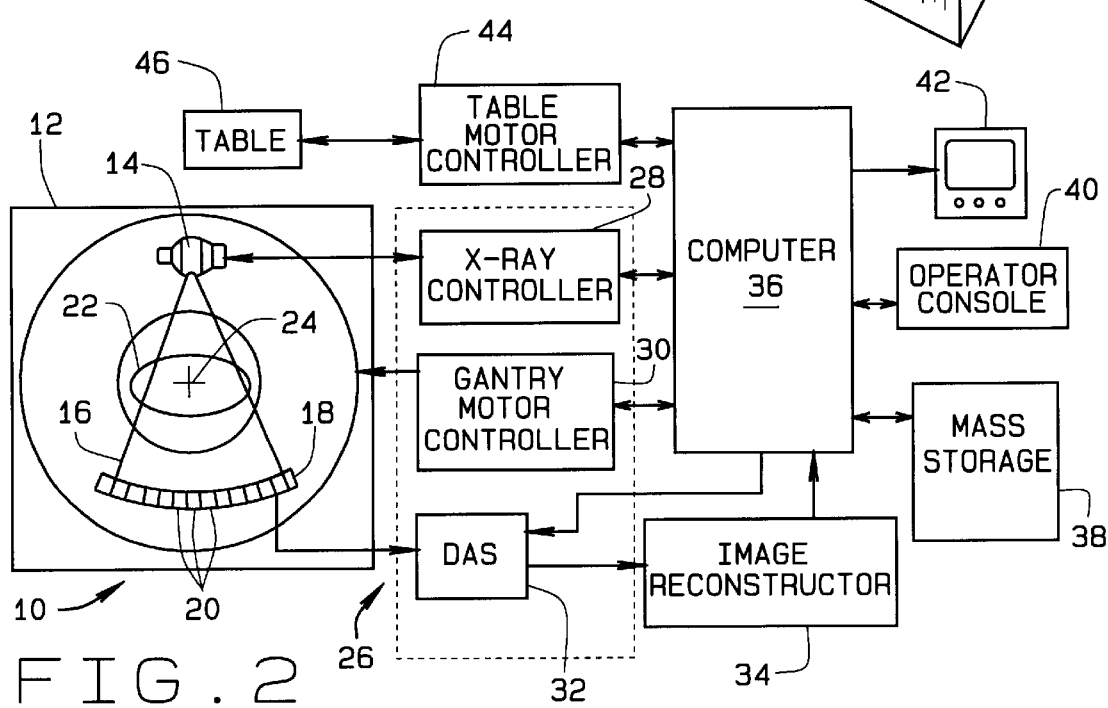
FIG. 2 is a block schematic diagram of the system illustrated in FIG. 1.

Referring to FIGS. 1 and 2, a computed tomographic (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
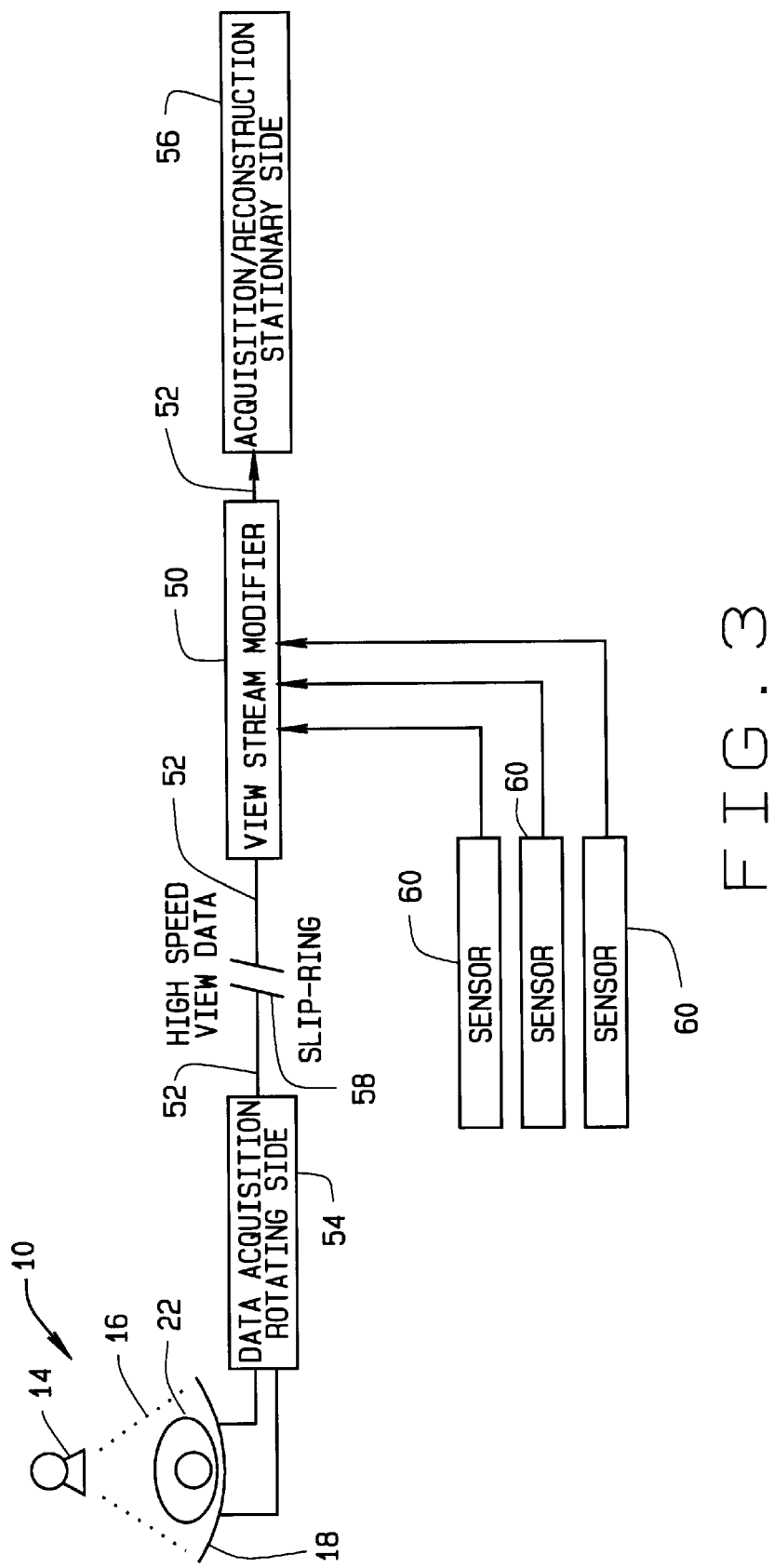
FIG. 3 is a block schematic diagram of an acquisition system embodiment of the present invention that integrates dynamic compensation information into a view stream.

In one exemplary embodiment of the present invention and referring to FIG. 3, a view stream modifier 50 is provided in a view stream path 52 between a rotating side portion 54 of DAS 32 and a data acquisition/recovery system 56 that includes a stationary side portion of DAS 32 and image reconstructor 34. The division of components by slip ring 58 is convenient for implementation of this embodiment, but otherwise is only exemplary. View stream modifier 50 is in electrical communication with one or more dynamic parameter sensors 60 that provide electrical indications of data other than attenuation measurements. For example, sensors 60 include a gantry/table position sensor and a physiological data sensor in one embodiment. Other embodiments have different numbers of sensors 60 and/or different types or combinations of sensors 60. In one embodiment, an object 22 is scanned with a beam of radiation 16 from CT imaging system 10 to produce a view stream communicated via view stream path 52. One or more dynamic parameters related to either or both of object 22 or CT imaging system 10 are sensed. View stream modifier 50 integrates information relating to one or more of the sensed dynamic parameters into the view stream.

In one embodiment, CT imaging system 10 is used to capture physiology in a particular state without motion artifacts. For example, sensors 60 include an EKG sensor and a respiration sensor to sense an EKG parameter and a respiration parameter, respectively. These dynamic parameters are integrated into the view stream and temporally related with attenuation measurement data in the view stream. For example, dynamic parameters are sampled at particular times and multiplexed into the view stream in corresponding, predefined time slots, and/or explicit time indications are included with either or both of the dynamic information and the attenuation data. Stationary side acquisition/recovery system 56 receives sensor 60 information in the view stream along with attenuation measurements. Both the attenuation measurements and the temporally-related dynamic information are used by acquisition/recovery system 56 in a modified reconstruction algorithm to select particular segments of view data for image reconstruction. The view data segments selected are those that minimize motion artifacts in reconstructed images and therefore compensate for motions of a patient 22. For example, in one embodiment, the reconstruction algorithm utilizes only segments of view data corresponding to a relatively stationary portion of a cardiac cycle to reconstruct an image of a heart. Useful segments for compensated reconstruction are readily determined by their temporal relationships to R-peaks in an EKG parameter cycle. In another embodiment, motion-induced artifacts resulting from patient respiration are reduced by utilizing view data having a specified relationship with portions of the patient's respiration cycle.

In one embodiment, patient information acquired by one or more sensors 60 is also displayed, for example, on CRT display 42, in conjunction with corresponding reconstructed images displayed on the same (or a separate) display.

Figure 4:
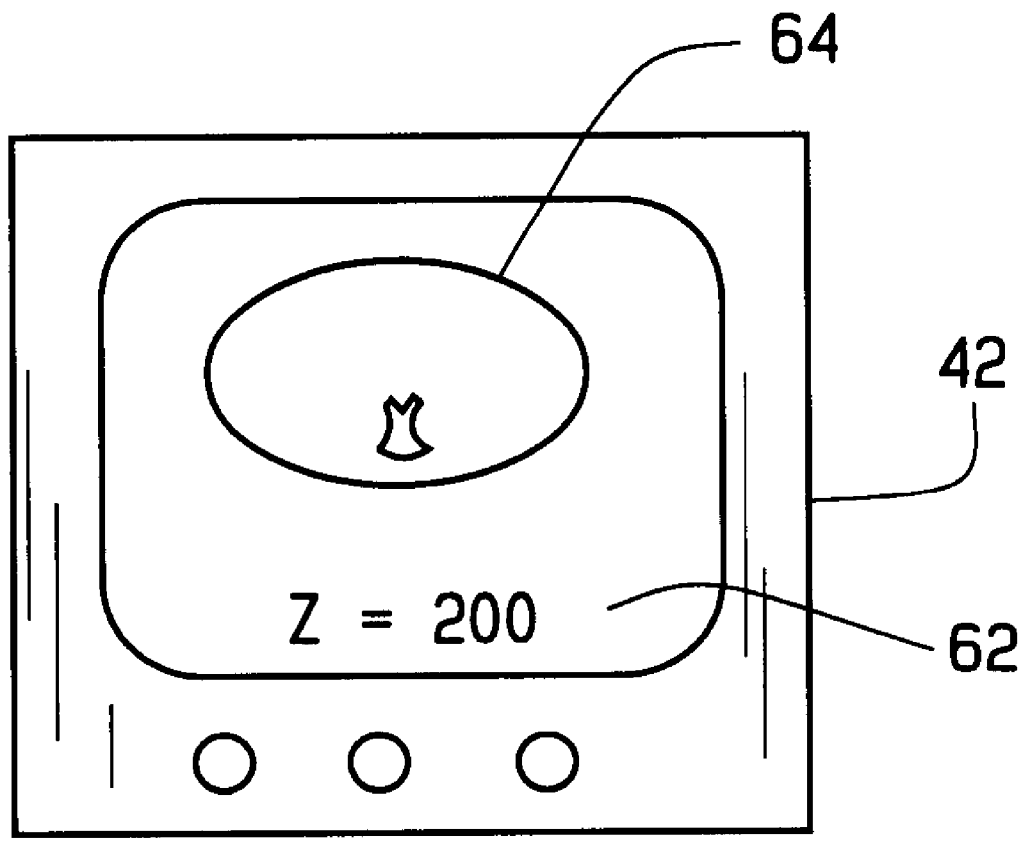
FIG. 4 is an illustration of a compensated image being displayed in conjunction with corresponding temporally-related dynamic information.

In another embodiment of the present invention, imaging system 10 is configured to provide helical scans having variable pitch and/or table 46 translation speed so that a radiologist is able to scan different locations of a body using different pitches. Because a dynamic parameter related to a table position parameter is integrated into a view stream by view stream modifier 50, separate helical scans for these different body locations are not required. The integrated dynamic parameter and its temporal relationship with the attenuation data in the view stream are used by a reconstruction algorithm in stationary side acquisition/reconstruction system 56 to reconstruct images with compensation for speed changes. In addition to eliminating the need for separate helical scans, this embodiment also provides information to produce acceptable images during translation speed changes and to determine actual image locations. In one embodiment, and as shown in FIG. 4 these determined image locations 62 are displayed in conjunction with corresponding reconstructed images 64 on CRT display 42.

In yet another embodiment, CT imaging system 10 is used in a fluoro application, and sensors 60 provide dynamic positional parameters relating to table 46 and gantry 12. A real-time reconstruction algorithm is used by stationary-side acquisition/reconstruction system 56 to produce images as a patient is scanned. Table 46 and/or gantry 12 in this embodiment are manually moveable so that a radiologist is able to manually move table 46 and/or tilt gantry 12 during a scan. Stationary-side acquisition/reconstruction system 56 is configured to use the dynamic positional parameters, the attenuation data included in the view stream, and their temporal correlation to reconstruct compensated images. Thus, blurring is reduced during manual gantry 12 tilting and/or movement of table 46. In one embodiment, gantry 12 tilt information and/or table location information is displayed in conjunction with a corresponding compensated image.

Although position and/or tilt sensors are used in some of the above embodiments to sense dynamic information parameters, sensors detecting changes or derivatives (including first or second derivatives) of these parameters are considered as being entirely equivalent for purposes of this invention. Changes or derivatives need only to be summed or integrated from known initial conditions (e.g., a starting position or tilt) to provide the same dynamic parameter information as the corresponding position and/or tilt sensors. In principle, changes and first or second derivatives of an EKG signal and/or a respiration signal could also be used instead of the signals themselves in other embodiments.

The above-described embodiments are intended to be exemplary only. However, it will be seen that these embodiments provide convenient methods and apparatus for compensating conventional CT images for dynamic changes in a patient or in a scanning environment, utilizing a view stream to provide the compensation information.

The CT system described herein is a "third generation" system in which both the x-ray source and detector rotate with the gantry. Many other CT systems including "fourth generation" systems wherein the detector is a fall-ring stationary detector and only the x-ray source rotates with the gantry, may be used if individual detector elements are corrected to provide substantially uniform responses to a given x-ray beam. Thus, while the invention has been described in terms of various specific embodiments, those skilled in the art will recognize that the invention can be practiced with modification within the spirit and scope of the claims.

What is claimed is:

1. A method for imaging an object with a computed tomographic (CT) imaging system comprising the steps of:
   scanning an object with a beam of radiation from a CT imaging system to produce a view stream including attenuation data for the object being scanned;
   sensing one or more dynamic parameters relating to at least one of the object being scanned and the CT imaging system; and integrating information relating to the one or more sensed dynamic parameters into the view stream.

2. A method in accordance with claim 1 further comprising the step of temporally relating the integrated information with the attenuation data in the view stream.

3. A method in accordance with claim 2 wherein the object is a patient, and the one or more dynamic parameters are selected from the group consisting of an EKG signal parameter, and a respiration parameter.

4. A method in accordance with claim 2 and further comprising the step of reconstructing an image of the object, including compensating for motions of the object using the temporally-related integrated information in the view stream.

5. A method in accordance with claim 4 wherein the one or more dynamic parameters includes an EKG signal, and compensating for motions of the object using the temporally related integrated information in the view stream comprises the step of selecting segments of view data corresponding to relatively stationary periods of a heart utilizing the temporally related integrated information.

6. A method in accordance with claim 2 wherein the CT imaging device comprises a table configured to support the object in a gantry, a radiation source emitting the beam of radiation and a detector, the radiation and detector being mounted on opposite sides of the gantry, and the one or more dynamic parameters are selected from the group consisting of gantry tilt position, table location, and changes and first and second derivatives thereof.

7. A method in accordance with claim 6 wherein the one or more dynamic parameters includes a member selected from the group consisting of gantry tilt position and changes and first and second derivatives thereof, and said method further comprises the steps of tilting the gantry during the scanning step, and reconstructing a fluoroscopic image of the object, including compensating for tilting motions of the gantry using the temporally-related integrated information in the view stream.

8. A method in accordance with claim 6 wherein the one or more dynamic parameters includes a member selected from the group consisting of table location and changes and first and second derivatives thereof, the object is helically scanned, and further comprising the steps of varying the helical pitches at which the object is scanned during a scan, and reconstructing images of different locations of the object scanned at different helical pitches, including compensating for the different helical pitches using the temporally-related integrated information in-the view stream.

9. A method in accordance with claim 2 further comprising the steps of reconstructing an image of the object, and displaying at least a portion of the temporally-related integrated information corresponding to the reconstructed image in conjunction with the reconstructed image.

10. A computed tomographic (CT) imaging system for imaging an object configured to:

scan an object with a beam of radiation to produce a view stream including attenuation data for the object being scanned;

sense one or more dynamic parameters relating to at least one of the object being scanned and the CT imaging system; and integrate information relating to the one or more sensed dynamic parameters into the view stream.

11. A system in accordance with claim 10 further configured to temporally relate the integrated information with the attenuation data in the view stream.

12. A system in accordance with claim 11 wherein the one or more dynamic parameters are selected from the group consisting of an EKG signal parameter, and a respiration parameter.

13. A system in accordance with claim 11 further configured to reconstruct a compensated image of the object, including compensation for motions of the object using the temporally-related integrated information in the view stream.

14. A system in accordance with claim 13 wherein the one or more dynamic parameters includes an EKG signal, and said system being configured to compensate for motions of the object using the temporally related integrated information in the view stream comprises said system being configured to select segments of view data corresponding to relatively stationary periods of a heart utilizing the temporally related integrated information.

15. A system in accordance with claim 11 further comprising a table configured to support the object in a gantry, a radiation source emitting the beam of radiation and a detector, the radiation and detector being mounted on opposite sides of the gantry, and the one or more dynamic parameters are selected from the group consisting of gantry tilt position, table location, and changes and first and second derivatives thereof.

16. A system in accordance with claim 15 wherein the one or more dynamic parameters includes a member selected from the group consisting of gantry tilt position and changes and first and second derivatives thereof, and said system is further configured to tilt the gantry during the scanning step, and to reconstruct a compensated fluoroscopic image of the object, including compensation for tilting motions of the gantry using the temporally-related integrated information in the view stream.

17. A system in accordance with claim 15 wherein the one or more dynamic parameters includes a member selected from the group consisting of table location and changes and first and second derivatives thereof, said system being configured to helically scan the object at the varying helical pitches during a scan, and to reconstruct compensated images of different locations of the object that are scanned at different helical pitches, including compensation for the different helical pitches using the temporally-related integrated information in the view stream.

18. A system in accordance with claim 11 further configured to reconstruct an image of the object, and to display at least a portion of the temporally-related integrated information corresponding to the reconstructed image in conjunction with the reconstructed image.

* * * * *